United States Patent [19]

Saito et al.

[11] Patent Number: 4,707,167
[45] Date of Patent: Nov. 17, 1987

[54] AIR STERILIZATION FILTER

[75] Inventors: Kenichiro Saito, Tokyo; Chikao Kanaoka, Kanazawa; Shigeyuki Aoyama, Tokyo, all of Japan

[73] Assignee: Aoki Corporation, Osaka, Japan

[21] Appl. No.: 901,376

[22] Filed: Aug. 28, 1986

[30] Foreign Application Priority Data

Sep. 10, 1985 [JP] Japan ................... 60-198626

[51] Int. Cl.$^4$ .............................. B01D 35/06
[52] U.S. Cl. ...................... 55/267; 55/279; 55/385 A; 55/499; 55/521; 55/523
[58] Field of Search .......... 55/132, 267, 279, 360, 55/385 A, 497, 499, 521, 523

[56] References Cited

U.S. PATENT DOCUMENTS

| | | | |
|---|---|---|---|
| 2,628,083 | 2/1953 | Rense | 55/279 X |
| 2,735,509 | 2/1956 | Fields | 55/132 |
| 3,237,382 | 3/1966 | Berly | 55/279 X |
| 3,999,964 | 12/1976 | Carr | 55/499 X |
| 4,342,574 | 8/1982 | Fetzer | 55/267 X |
| 4,357,150 | 11/1982 | Masuda et al. | 55/132 X |
| 4,440,553 | 4/1984 | Helmus et al. | 55/279 X |
| 4,509,958 | 4/1985 | Masuda et al. | 55/521 X |
| 4,608,063 | 8/1986 | Kurokawa | 55/267 X |
| 4,610,706 | 9/1986 | Nesher | 55/497 |
| 4,630,530 | 12/1986 | Eckstrom et al. | 55/279 X |

FOREIGN PATENT DOCUMENTS 22883 2/1977 Japan ................... 55/385 A

Primary Examiner—Robert Spitzer
Attorney, Agent, or Firm—Spencer & Frank

[57] ABSTRACT

An air sterilization filter for the containment of leakage prevention of biologically contaminated air in space for a biotechnological performance, such as a genetic engineering work. The filter comprises a heat durable sheet filter for collecting microorganisms suspended in air and a heater for heating the sheet filter and sterilizing the collected microorganisms. The filter of the invention is also useful for providing a clean room.

15 Claims, 14 Drawing Figures

FIG._1
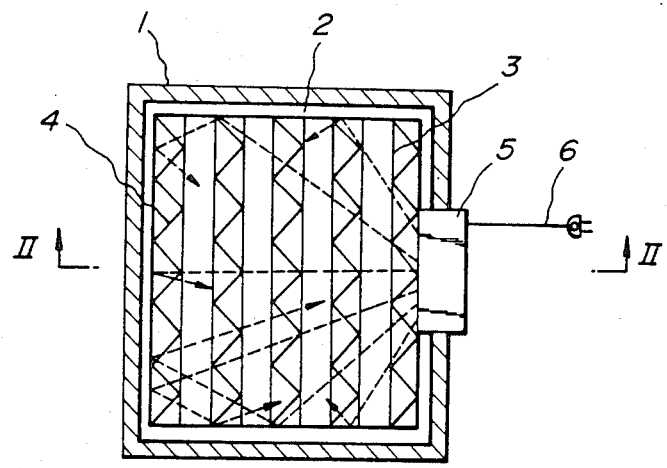
FIG._2
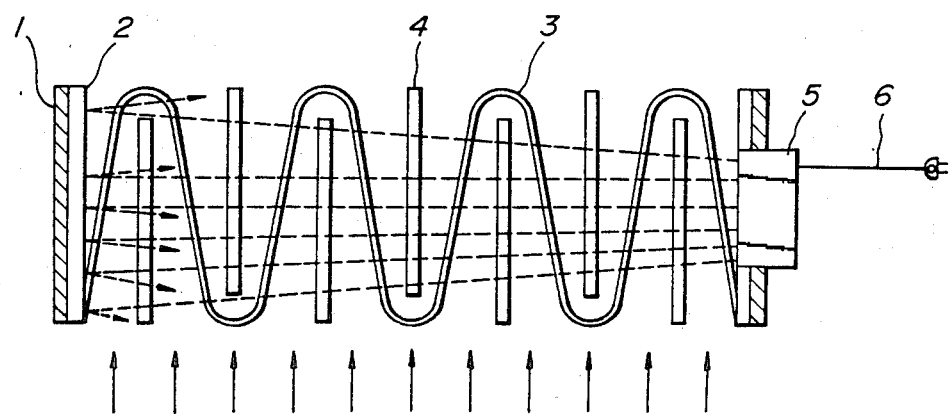

FIG_3
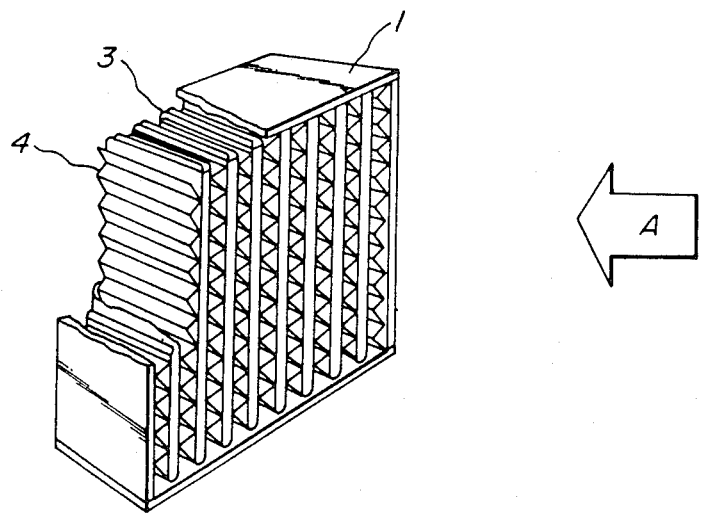
FIG_4
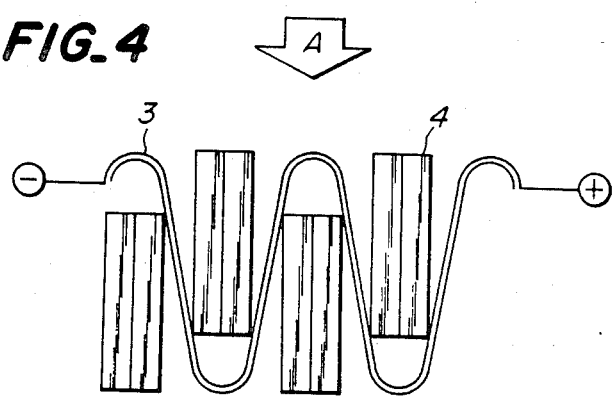
FIG_5
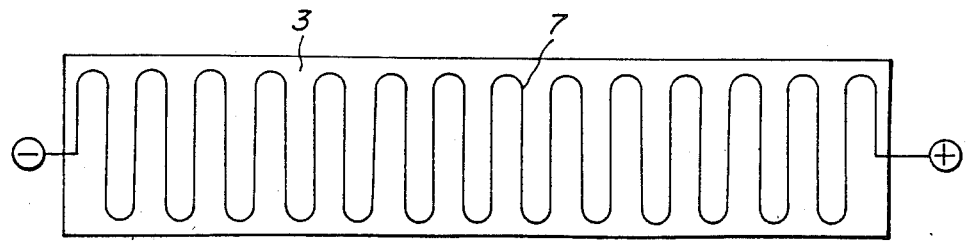

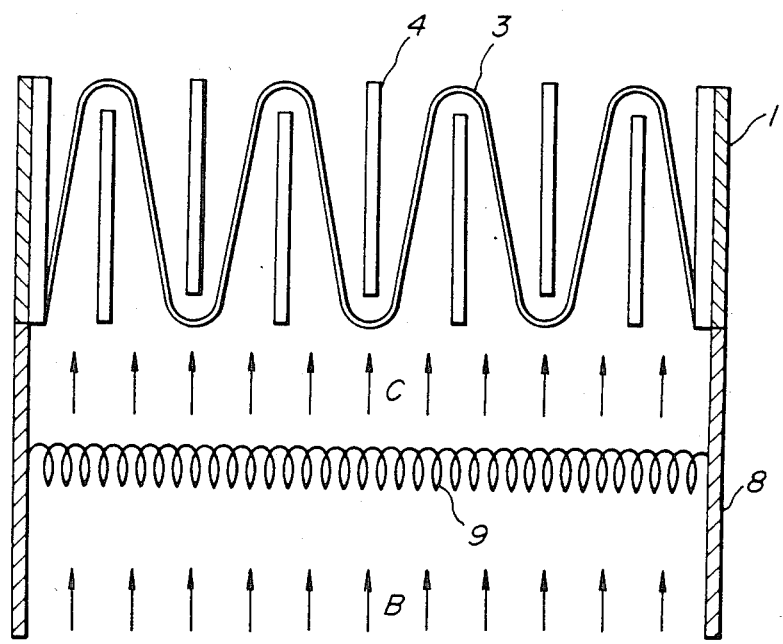
FIG_10

FIG_11
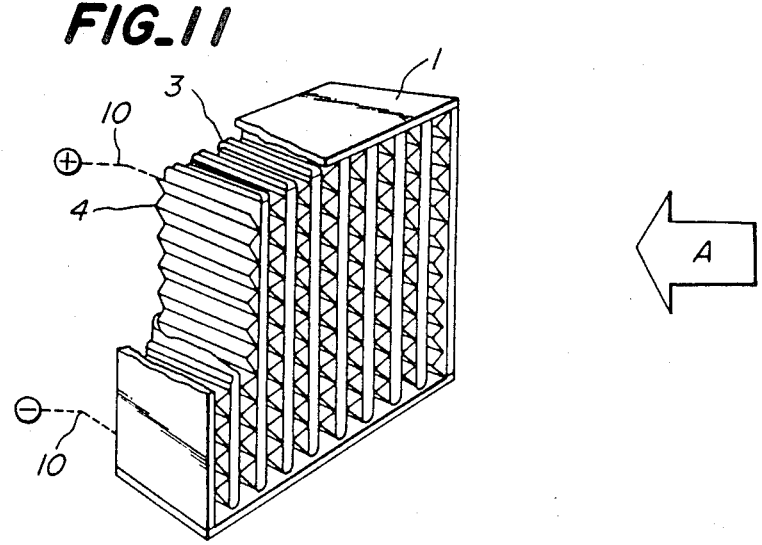
FIG_12
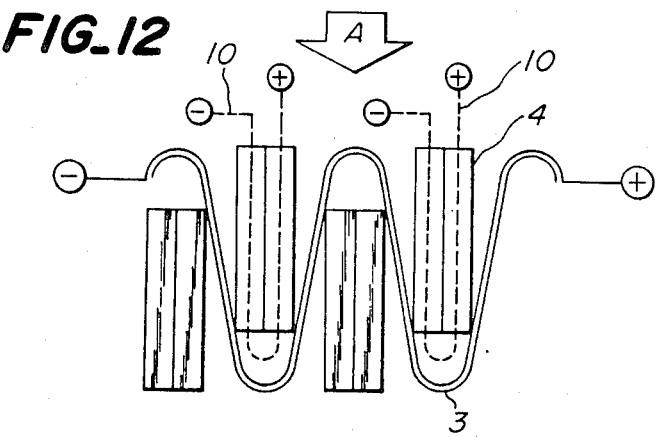
FIG_13
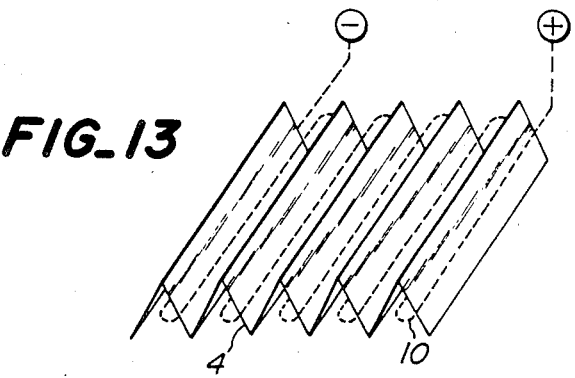

FIG_14
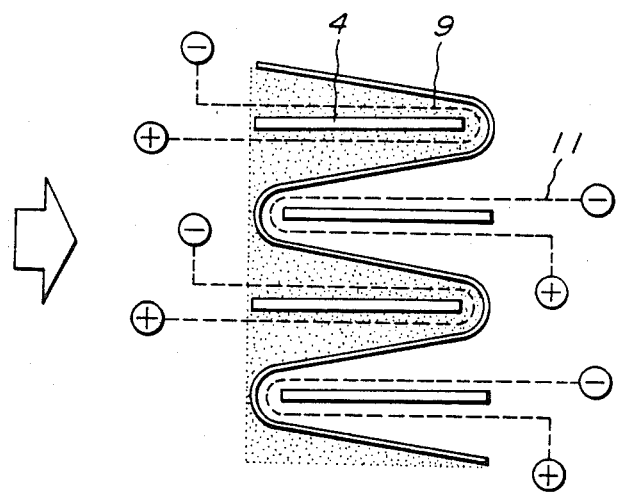

4,707,167

AIR STERILIZATION FILTER

BACKGROUND OF THE INVENTION

1. Field of the Invention

The present invention relates to an air sterilization filter to be provided in a passage for evacuating air from biologically contaminated space, or feeding air into a clean space where biological work is carried out, such as a containment laboratory in the biotechnological field and the like.

2. Related Art Statement

A known air filter of this kind is the so-called HEPA filter, i.e., high efficiency particulate air filter, which can physically collect fine dust particles and microorganisms, such as bacteria, virus, etc. which are suspended in the air and have particle size diameter of at least 0.3 μm, with a filtration efficiency of 99.97% or more, only by passing air through the microporous filter.

Accordingly, with conventional HEPA filters as described above, the collection of dust particles, microorganisms, such as bacteria, virus, etc, suspending in the air is not always effected with 100% certainity, entailing possible leakages, even through they may be very little, and further a phenomenon can occur such that particles once collected by the filter are dispersed again.

SUMMARY OF THE INVENTION

Differing from abiotic fine particles, such as dust, etc., biological microorganisms, such as bacteria, virus and the like, dealt with in the recently developed biotechnological field have a possibility of creating a biohazard or in some cases bring about fear that even human life may be endangered, so that maximum containment, i.e., contaiment with 100% certainty of biological microorganisms is required, as well as a space with 100% biological cleanliness.

Furthermore, in the case where a biologically contaminated filter is exchanged, there is involved also a problem of contamination of workers and environment.

It is an object of the present invention to satisfy the above-mentioned requirement and at the same time eliminate the aforesaid problem.

It is a further object of the present invention to provide an air sterilization filter which allows no microorganisms to pass through alive, and which is empolyable in a biohazard prevention system as well as a clean room.

It is yet another object of the present invention to impart a sterilizing ability to the HEPA filter without impairing its performance such as filtration efficiency.

The object of the present invention is attained by an air sterilization filter to be provided in a passage connecting a space for a biotechnological performance with the outside ambience, which comprises a sheet filter to collect microorganisms suspended in an airflow which is provided with a heating means to heat said sheet filter to sterilize the collected microorganisms. More particularly, the present invention is an air sterilization filter to filtrate air flowing through a passage connecting a space for a biotechnological performance with the outside ambience, which comprises a filter box having an outer frame fitted in said passage, a sheet filter with a flexuously pleated configuration fixed across said passage in the filter box, and a plurality of separators each inserted into every pleat space of the sheet filter, and which is provided with a heating means for heating the sheet filter to a temperature of at least 80° C. (176° F.) to sterilize microorganisms carried by the air.

As a result of an authoritative experimentation using polivirus as an indicator, it has been found that objective microorganisms, such as bacteria, virus, etc., handled in biotechnology can be substantially completely killed in a very short period of time by heating at 80° C. (176° F.). Therefore, by providing a heating means on or near a sheet filter, to heat the sheet filter to 80° C. (176° F.) or higher, microorganisms, i.e., bacteria, virus, etc., which are collected and dwell on the heated sheet filter for a significant period of time can be sterilized with 100% certainty, so that according to the present invention, a containment or leakage prevention with 100% certainty is achievable without causing any biohazard or biological pollution of the environment, while a biologically 100% clean space is also obtainable when it is used in an air feeding passage.

Moreover, since a filter according to the present invention can sterilize, by means of heating, entire microorganisms, such as bacteria, virus, etc., which have been collected on the filter, a fear of contamination of workers and the environment during sheet filter exchanging can be eliminated.

BRIEF DESCRIPTION OF THE DRAWINGS

The preferred embodiments of the invention will now be described by way of example with reference to the accompanying drawings in which:

FIG. 1 is a sectional elevation of a first embodiment of the present invention;

FIG. 2 is a sectional view taken on a line corresponding with II—II in FIG. 1;

FIG. 3 is a bird's eye perspective view of a second embodiment of the present invention with a part broken away;

FIG. 4 is a partially schematic sectional view of the filter shown in FIG. 3;

FIG. 5 is a plan view in a stretched form of the folded filter shown in FIG. 4;

FIG. 10 is plan sectional view of FIG. 9;

FIG. 11 is a bird's eye perspective view of a fifth embodiment of the present invention with a part broken away;

FIG. 12 is a partially schematic sectional view of the filter shown in FIG. 11;

FIG. 13 is a bird's eye view of the separator shown in FIG. 11; and

FIG. 14 is a partially sectional schematic view of a preferred embodiment of the present invention.

DESCRIPTION OF THE PREFERRED EMBODIMENTS

Figure 6:
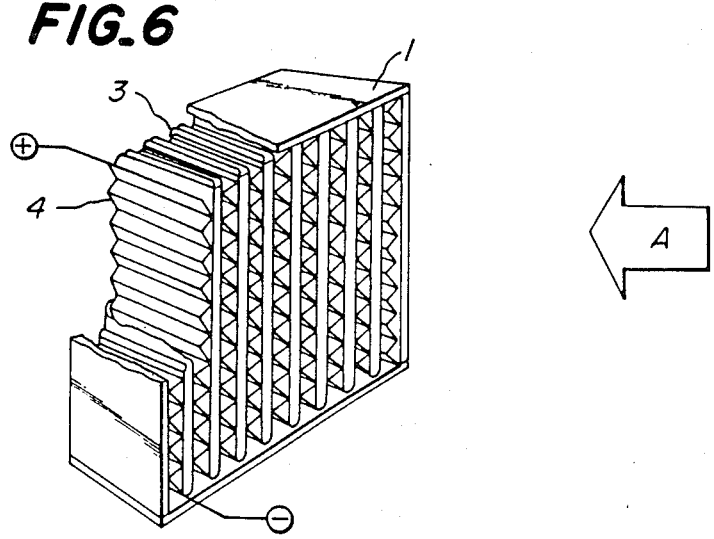
FIG. 6 is a bird's eye perspective view of a third embodiment of the present invention with a part broken away.

In FIGS. 1 and 2 illustrating an air filter provided with a high frequency heating means, a filter box is composed of an outer frame 1, the inside surfaces of which are lined with a high frequency reflective plate 2, and in the inside space of which a microporous sheet filter 3 pleated into a flexuous configuration is provided across the air passage, together with accordion pleated separators 4, each inserted contiguously into every pleat space of the sheet filter. On a side wall of the filter box is provided an opening into which is fitted a high frequency irradiation unit 5 having a cord 6 for connecting with an electric source (not shown).

Upon connection of the cord 6 with an electric source, high frequency energy is emitted from high frequency irradiation unit 5 and reflected by reflective plate 2, as shown by dotted lines in FIGS. 1 and 2, whereby the whole air passage in the filter box as well as the sheet filter itself can be heated. Accordingly, microorganisms, such as bacteria, virus and the like, carried by air flowing into the filter in the direction shown by solid arrows in FIG. 2 and collected on the sheet filter can be sterilized.

Further, FIGS. 3–5 illustrate a second embodiment of the invention wherein the sheet filter is provided with a heating means. Throughout all Figures of the drawing, corresponding reference numerals show like parts. As shown in FIG. 3, reflective plate 2 is not required in this case.

In the second embodiment, an electrothermal filament 7 is fixed, lying in a zigzag line, on the sheet filter (filter paper) 3 as shown in the stretched form in FIG. 5, so that the sheet filter 3 can be heated by application of an electric current to electrothermal filament 7. As the electrothermal filament 7, use may be made of, e.g., a Nichrome filament or a printed electrothermal circuit on sheet filter 3.

In this embodiment, since sheet filter 3 is also heated upon application of an electric current to electrothermal filament 7, when air flowing into the filter as shown by arrows A in FIGS. 3 and 4 passes through sheet filter 3, microorganisms, e.g., bacteria and virus, are collected by the sheet filter 3 and at the same time sterilized on the hot sheet filter.

Figure 7:
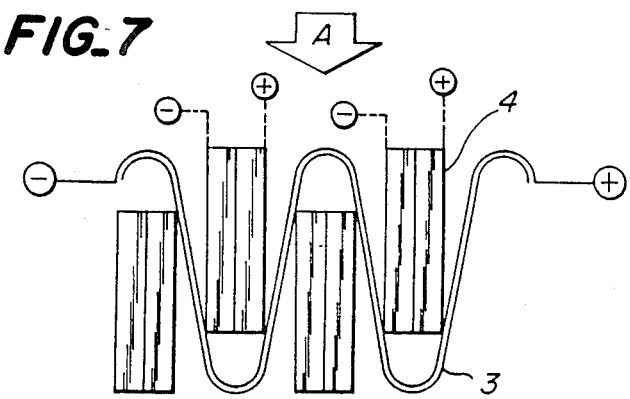
FIG. 7 is a partially schematic sectional view of the filter shown in FIG. 6.
Figure 8:
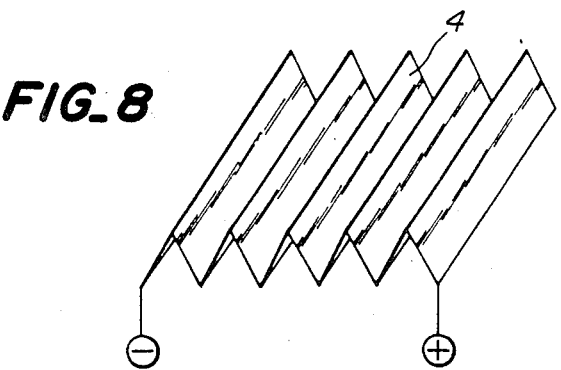
FIG. 8 is a bird's eye view of the separator shown in FIG. 7.

Furthermore, FIGS. 6–8 illustrate a third embodiment of the invention wherein the separator is provided with a heating means.

In this embodiment, separator 4 may be made of an electric resistant heating element, e.g., a Nichrome plate, to which an electric current can be applied, or made of a non-conducting material provided with an electrothermal filament or printed circuit laid thereon.

In this case, upon application of an electric current to separator 4, the separator 4 is heated and at the same time adjacent sheet filter 3 is also heated by the hot separator, so that microorganisms, e.g., bacteria, virus, etc. carried by air flowing in the direction shown by arrow A can be sterilized.

Figure 9:
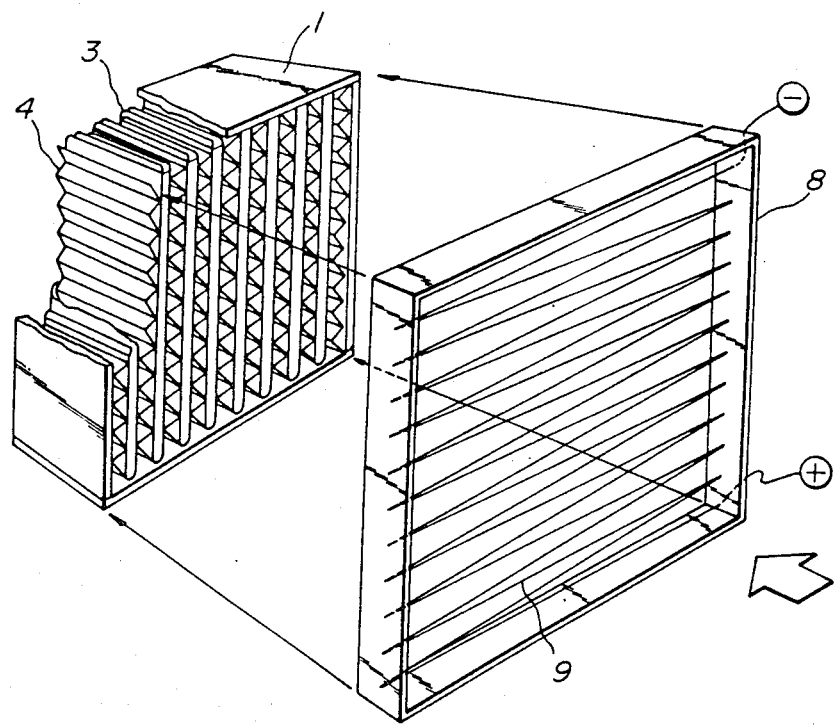
FIG. 9 is a bird's eye perspective view of a fourth embodiment of the present invention with a part broken away.

Furthermore, FIGS. 9 and 10 illustrate a fourth embodiment of the invention wherein a heating means is provided in an air flowing-in passage.

Namely, on the air entering side of the outer frame 1 of the filter box is conjointly provided an electric heater frame 8 which has a heating grid consisting of electrothermal coil filaments 9 stretched with a uniform distribution over the area perpendicular to the airflow.

In this embodiment, upon application of an electric current to the heating grid, the electrothermal filaments 9 of the heating grid are red heated whereby cold air flowing in as shown by arrow B in FIG. 10 is heated to a high temperature when passing through the heating grid, so that microorganisms, e.g., bacteria, virus, etc. are thereby sterilized. Then, the hot air flows into the filter as shown by arrow C and is filtrated. In this case, even if survived bacteria, virus or the like remain in the airflow after having passed through the heating grid, these microorganisms are collected and eventually sterilized on the sheet filter, since the sheet filter itself has been heated by the hot airflow and the radiant heat from the grid.

Furthermore, FIGS. 11–13 illustrate a fifth embodiment of the invention wherein electrothermal filaments are provided in the separators.

Namely, in those Figures, the electrothermal filaments 10 shown by dotted lines are laid in furrows of the pleated separators 4.

Since upon application of an electric current to electrothermal filaments 10, the adjacent separator 4 and sheet filter 3 are heated, microorganisms carried by airflow coming into the filter as shown by arrow A can be sterilized as the other embodiments explained hereinabove.

FIG. 14 illustrates a preferred embodiment of the present invention which is provided with a safety device. The safety device comprising safety electrothermal filaments 11 is provided behind the sheet filter on the air exit side in addition to the heating means 9 provided on the air entering side. The electric circuit is so designed that the safety device can work independently. The safety device heats up air flowing out of the filter and serves to prevent microogranisms from passing through alive, even in case of an accident such as breakage of the sheet filter, short circuiting of the electric heating elements and the like.

Sheet filters to be employed in the present invention are composed of heat durable materials which can withstand a high temperature of at least 150° C. (302° F.), preferably exceeding about 200° C. (392° F.). As such materials, mention may be made of woven or nonwoven fabrics of inorganic fibers, such as glass fibers, quartz fibers, silicon carbide fibers, mineral fibers, carbon fibers and the like, and heat-resistant organic fibers such as aramid fibers, for example, polymetaphenylene-isophthalamide and polyparaphenylene-terephthalamide; porous films made of heat-resistant organic materials such as polytetrafluoroethylene and the like; and ceramic sintered microporous bodies and the like.

Sheet filters specifically designed as HEPA filters in view of appropriate filtration efficiency, porosity, air-permeability, particulate adhesivity, etc. made from a material as described above, for example, a fiberglass mat, are commercially available and such HEPA filters capable of collecting fine particulate having a particle size in diameter of at least 0.3 $\mu$m with a filtration efficiency of at least 99.97% are most preferably used in the present invention.

The separator employed in the filter according to the present invention serves to separate contiguous pleats of sheet filter and also to guide and arrange airflow. As a material for the separator, in the case where the separator itself is not used as a heating means, metallic materials, e.g. aluminum, which have excellent heat-conductivity can be recommended so as to extend the thermal energy emitted from the heating means to the whole heating zone. On the other hand, when the separator itself is used as an electric heating means, it may be formed from either an electrothermal material to function as a heating element, or a non-conducting material, such as a synthetic resin, with an electrothermal layer, filament or circuit laid thereon. In the case where electric heating elements are provided in contact with or adjacent to separators, it is preferred that the separators, at least their parts facing the heating element, are laminated with an insulation film, to prevent short circuiting or sparking between electric heating elements.

The heating means can be adopted suitably from any conventional means, such as high frequency, electric resistance, ultra-red ray and the like heater. The temperature applied to the sheet filter by the heating means is generally at least about 80° C. (176° F.), preferably at least about 121° C. (250° F.) and at the highest below the thermal deformation or transformation temperature of the sheet filter material employed. In this specification and appended claims, the term "thermal deformation or transformation temperature of the sheet filter material" is to be understood to mean a temperature at which the sheet filter material undergoes physical deformation or chemical transformation, such as significant thermal expansion or contraction, softening, plastic deformation, melting, sublimation, carbonization by oxidation, decomposition, or the like.

By application of a temperature adequately selected from the above temperature range on the sheet filter, the microorganisms collected on the sheet filter can all be sterilized, while the filtering properties and performance of the sheet filter are not impaired, so that a perfect air sterilization filtration is achieved.

Further, the engineering design for providing a suitable heating means, such as the capacity of the high frequency irradiation unit, material and dimension of electric heating elements, and the like, will be readily performed by those skilled in the art.

Because of the outstanding advantages mentioned above, the air sterilization filters of the present invention are useful for biohazard prevention, in particular, for the purpose of a maximum containment or leakage-prevention of biologically contaminated air such as in a laboratory or plant for genetic engineering in the biotechnological field. Additionally, the filters according to the present invention are also preferably employable in operations which require a clean room or dustless environment, e.g., for an experiment or manufacture of pharmaceuticals and foodstuffs; medical treatments; manufacture of electronic devices such as semi-conductor devices; and the like.

While there has been shown and described the preferred embodiments of the present invention, it will be obvious to those skilled in the art that various alterations and modifications thereof can be made without departing from the scope of the invention as defined by the following claims.

What is claimed is:

1. An air sterilization filter for installation in a passageway between an enclosure wherein biological work is carried out and a space external thereto, comprising
    a filter box having interior walls surrounding said passageway;
    a sheet filter having a flexously pleated configuration defining a plurality of pleat spaces, said sheet filter being fixed to said interior walls and extending across said passageway;
    a plurality of separators located in the pleat spaces of said sheet filter; and
    heating means located inside said filter box for heating said sheet filter to a temperature between 80° C. and the thermal deformation or transformation temperature of the material comprising said sheet filter, said temperature being sufficient to sterilize micoorganisms carried by the air within said passageway.

2. A filter as claimed in claim 1, wherein the interior walls of said filter box are lined with a high frequency reflective plate, and wherein said filter box is provided on an interior wall with a high frequency irradiation unit, said high frequency irradiation unit emitting high frequency energy across said passageway.

3. A filter as claimed in claim 1, wherein said heating means comprises an electrothermal filament attached to said sheet filter, said sheet filter being heated when an electric current flows through said filament.

4. A filter as claimed in claim 3, wherein said separators are laminated with an insulation film, said separators and said electrothermal filament being in a facing relationship with respect to each other.

5. A filter as claimed in claim 1, wherein said separators are made of an electric resistant heating material, an electric current passing through said separators constituting said heating means.

6. A filter as claimed in claim 1, wherein said separators are made of a non-conducting material, and said heating means comprises an electrothermal filament attached to said separators.

7. A filter as claimed in claim 1, wherein said heating means is provided in said passageway, said heating means being located so that air flows from said heating means toward said sheet filter.

8. A filter as claimed in claim 7, wherein said heating means comprises a heating grid consisting of electrothermal filaments stretched over an area perpendicular to said airflow, said sheet filter being heated when an electric current flows through said filaments.

9. A filter as claimed in claim 1, wherein said separators are accordion-pleated.

10. A filter as claimed in claim 9, wherein said pleated-separators have furrows, and wherein said heating means comprises electrothermal filaments laid in said furrows.

11. A filter as claimed in claim 1, wherein electrothermal filaments are provided in said passageway in a position such that air flows from said sheet filter toward said filaments, said filaments heating air flowing from said sheet filter toward said filaments, whereby microorganisms are prevented from passing through said filter alive in the event of a malfunction of said sheet filter or heating means.

12. A filter as claimed in claim 1, wherein said sheet filter is heated to a temperature of at least 121° C.

13. A filter as claimed in claim 1, wherein said sheet filter is composed of a heat durable material which can withstand a temperature of at least 150° C.

14. A filter as claimed in claim 13, wherein said heat durable material is selected from the group consisting of inorganic fibers, heat resistant organic fibers and microporous films, and ceramic sintered microporous materials.

15. A filter as claimed in claim 1, wherein the sheet filter is a HEPA filter.

* * * * *